United States Patent [19]
Lazzara et al.

[11] Patent Number: 6,120,293
[45] Date of Patent: *Sep. 19, 2000

[54] ABUTMENT FOR A TEMPORARY TOOTH

[75] Inventors: Richard J. Lazzara, Lake Worth; Keith D. Beaty, Palm Beach Gardens, both of Fla.

[73] Assignee: Implant Innovations, Inc., West Palm Beach Gardens, Fla.

[*] Notice: This patent is subject to a terminal disclaimer.

[21] Appl. No.: 09/301,402

[22] Filed: Apr. 28, 1999

Related U.S. Application Data

[63] Continuation of application No. 08/337,387, Nov. 8, 1994, Pat. No. 5,899,695.

[51] Int. Cl.[7] .................................................... A61C 8/00
[52] U.S. Cl. ............................................................ 433/173
[58] Field of Search ................................... 433/172, 173, 433/174, 175, 176

[56] References Cited

U.S. PATENT DOCUMENTS

| | | |
|---|---|---|
| 4,758,161 | 7/1988 | Niznick . |
| 4,850,870 | 7/1989 | Lazzara et al. . |
| 4,850,873 | 7/1989 | Lazzara et al. . |
| 4,856,994 | 8/1989 | Lazzara et al. . |
| 4,955,811 | 9/1990 | Lazzara et al. . |
| 4,988,298 | 1/1991 | Lazzara et al. . |
| 5,006,069 | 4/1991 | Lazzara et al. . |
| 5,015,186 | 5/1991 | Detsch . |
| 5,030,096 | 7/1991 | Hurson et al. . |
| 5,035,619 | 7/1991 | Daftary . |
| 5,040,983 | 8/1991 | Binon . |
| 5,071,351 | 12/1991 | Green, Jr. et al. . |
| 5,073,111 | 12/1991 | Daftary . |
| 5,100,323 | 3/1992 | Friedman et al. . |
| 5,125,841 | 6/1992 | Carlsson et al. .............. 433/213 |
| 5,135,395 | 8/1992 | Marlin . |
| 5,145,371 | 9/1992 | Jorneus . |
| 5,145,372 | 9/1992 | Daftary et al. . |
| 5,154,612 | 10/1992 | Carlsson et al. . |
| 5,188,800 | 2/1993 | Green, Jr. et al. . |
| 5,209,659 | 5/1993 | Friedman et al. . |
| 5,209,666 | 5/1993 | Balfour et al. . |
| 5,213,502 | 5/1993 | Daftary . |
| 5,246,370 | 9/1993 | Coatoam . |
| 5,281,140 | 1/1994 | Niznick . |
| 5,292,252 | 3/1994 | Nickerson et al. . |
| 5,297,963 | 3/1994 | Daftary . |

(List continued on next page.)

FOREIGN PATENT DOCUMENTS 0 657 146 A1  6/1995  European Pat. Off. .

OTHER PUBLICATIONS

Exhibit C, a one–piece healing abutment made entirely of DELRIN™.
Exhibit A, a drawing of a healing abutment.
Exhibit B, an assembly drawing of a coping and the component drawings which comprise the coping assembly.
Perri, DDS, George et al., Single Tooth Implants, *CDA Journal*, vol. 17, No. 3, Mar. 1989.
DIA™ Dental Imaging Associates, Implamed—The Source, *The Anatomical Abutment System*, Copyright Date Oct. 9, 1991 on p. 10 (front cover, pp. 1–10, and back cover).
Lewis, S.G. et al., Single Tooth Implant Supported Restorations, Int'l. J.L. of Oral & Maxillofacial Implants, vol. 3, No. 1, pp. 25–30, 1988.
Lewis, S.G. et al., The "UCLA" Abutment, Int'l. J.L. of Oral & Maxollofacial Implants, vol. 3, No. 3, pp. 183–189, 1988.

*Primary Examiner*—Nicholas D. Lucchesi
*Attorney, Agent, or Firm*—Jenkens & Gilchrist

[57] ABSTRACT

Dental restoration components for use to make a replacement tooth which substantially mimics the emergence profile of a natural tooth comprising two parts, one being a core adapted for fixation subgingivally in the site of the natural tooth, and the other being an emergence-profiler guide which fits on the core and shapes the overlying gingiva to the desired emergence profile. Two sets of the components may be provided, one for use as a healing abutment, and the other for use as an impression coping.

32 Claims, 2 Drawing Sheets

U.S. PATENT DOCUMENTS

| | | |
|---|---|---|
| 5,316,476 | 5/1994 | Krauser . |
| 5,334,024 | 8/1994 | Niznick . |
| 5,336,090 | 8/1994 | Wilson, Jr. et al. . |
| 5,338,196 | 8/1994 | Beaty et al. . |
| 5,368,483 | 11/1994 | Sutter et al. . |
| 5,419,702 | 5/1995 | Beaty et al. . |
| 5,431,567 | 7/1995 | Daftary . |
| 5,476,383 | 12/1995 | Beaty et al. . |
| 5,492,471 | 2/1996 | Singer . |
| 5,651,675 | 7/1997 | Singer ................................ 433/172 |
| 5,662,476 | 9/1997 | Ingber et al. ..................... 433/213 |
| 5,674,069 | 10/1997 | Osorio ................................ 433/172 |
| 5,674,071 | 10/1997 | Beaty et al. ..................... 433/172 |
| 5,674,073 | 10/1997 | Ingber et al. ..................... 433/213 |
| 5,681,167 | 10/1997 | Lazarof ............................. 433/174 |

6,120,293

ABUTMENT FOR A TEMPORARY TOOTH

CROSS REFERENCE RELATED APPLICATIONS

This application is a continuation of U.S. Ser. No. 08/337,387, filed on Nov. 8, 1994 now U.S. Pat. No. 5,899,695.

This invention relates to the art of preparing dental restorations that closely replicate natural dentition in appearance, contour and dimensions, especially where the teeth emerge from the gums. More particularly, this invention addresses the task of providing an improved emergence profile for an artificial tooth which will closely replicate the emergence profile of the natural tooth that it replaces no matter what the size and shape of the emergence profile of that tooth may have been. The invention of this application is related to the invention of application Ser. No: 08/043,928 filed Apr. 8, 1993 and allowed Feb. 14, 1994, both applications being commonly owned.

BACKGROUND OF THE INVENTION

For artificial teeth (commonly called "dental restorations") closely to replicate the lost natural teeth that they replace the artificial teeth must appear to emerge from the gums with the same shapes and contours that natural teeth have as they emerge from the gums. The increasing availability of dental implants, particularly osseointegrated implants, to serve as artificial roots, has provided opportunities to address this problem using techniques for fabricating implant-supported restorations directly to implants. Such a technique is described in published articles which appeared in The International Journal of Oral & Maxillofacial Implants, Vol. 3, Number 1, 1988 at pages 25–26 "Single-Tooth Implant Supported Restorations" Lewis, S. G. et al., and Number 3, 1988 at pages 183–189 "The "UCLA" Abutment", Lewis, S. et al. A similar result using a different abutment is described in U.S. Pat. No. 4,988,298, which is owned by the Assignee of the present invention. The problem is incompletely addressed in U.S. Pat. No. 5,073,522 issued to Daftary Dec. 17, 1991.

In general, the existing techniques are done using components which function to expand a transmucosal opening from the round size of the implant to a larger round size that more nearly approximates the size of the tooth where it emerges from the gum. The above-mentioned application Ser. No. 08/043,928 teaches a method and means to expand a transmucosal opening from the round size of the implant to a larger non-round size that more nearly approximates the size and the shape of the tooth where it emerges from the gum. The present invention further improves the art with a system of interchangeable components which enables low cost and convenient replication of the emergence profiles of all the different sizes and shapes of human teeth.

GENERAL NATURE OF THE INVENTION

Generally, the invention provides a pair of substantially identical core abutments, one to be used to support a healing abutment, and the other to be used to support an impression coping, together with a set of identical pairs of anatomic emergence-profiler healing abutment and impression coping formers, or guides, which are interchangeably mountable on the core abutments. Each set replicates the emergence profile of one type of natural tooth—e.g: molar, premolar, bicuspid, incisor, etc. The core abutments are made of a rigid material that can be made in precise dimensions, such as titanium. The emergence-profiler abutment and coping formers or guides are made of a low cost moldable material, such as a plastics material (e.g: acrylic) that is acceptable for dental use, and are preferably disposable, so that they can be used or one patient only and can if necessary be modified at chair-side. The emergence-profiler abutment guides replicate the emergence profile of the tooth that is to be restored, but they are made so short that they need not have occlusive surfaces, and the core abutments used to support them are similarly shortened. The emergence-profiler coping guides may be similarly short, in fact they may be identical to their corresponding emergence-profiler abutment guides, but the core abutments used to support the emergence-profiler coping guides may be longer for engagement in the materials used to take impressions, and may be fitted with means to retain them in the impression material. The invention has as its principal object to provide low-cost, reliable and precise method and means to realize the invention of the above-mentioned application Ser. No. 08/043,928. Like the invention of that application, the invention of the present application can be used to make stone models and soft tissue models of a patient's case.

DETAILED DESCRIPTION OF THE DRAWINGS

Figure 1:
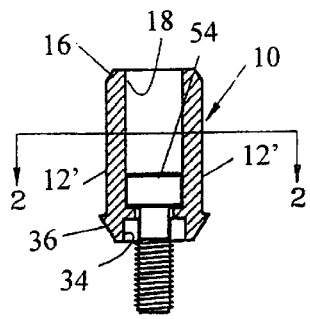
FIG. 1 is a longitudinal section through a core abutment according to the invention.
Figure 2:
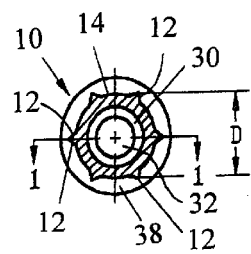
FIG. 2 is a transverse section through FIG. 1.
Figures 3, 7:
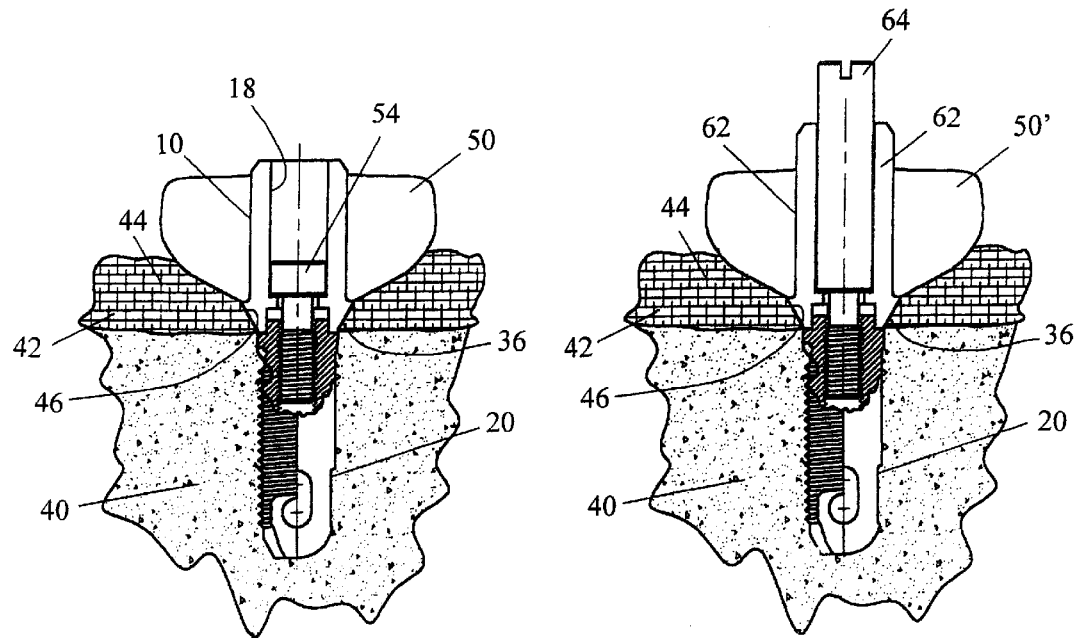
FIG. 3 is a side view of a healing abutment assembled on a dental implant.
FIG. 7 is a side view of a pick-up type transfer coping assembled on a dental implant.

Referring first to FIGS. 1 to 3, a core component 10 is generally tubular in form with an outer diameter "D" substantially the same as the diameter of the implant 20 (FIG. 3) on which it is to be mounted. Longitudinally-oriented ribs 12 are on the outer surface 14 which defines the diameter "D". Preferably, the ribs 12 have sharp edges 12', seen in FIG. 1. The ends 16 of the ribs at the supragingival end 18 of the core component are sloped toward the sharp edges. Six ribs are illustrated in FIG. 2, but the number of ribs can be different. In other structural respects that are illustrated in the drawings, the core components are similar to known abutments; that is, the transverse member 30 defining a screw hole 32 and the top surface of a hexagonal socket 34, and the expanded subgingival end 36 with its shoulder 38, are known features of existing abutments.

Figure 4:
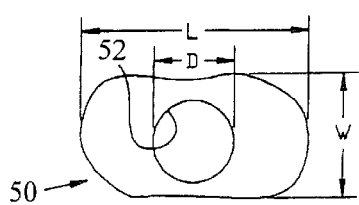
FIG. 4 is a top view of a emergence-profiler component of the invention.

In FIG. 3 the core component 10 is shown installed on a dental implant 20 which is fixed in bone 40 having overlying gingiva 42 with an aperture 46 giving access to the implant. As is the prevailing dental practice, the implant is substantially entirely encased in the bone, and the subgingival end 36 is mated to the implant, through the aperture, within the gingiva, at the junction of the gingiva and the bone. The emergence profile to be given to the aperture 46 through the gingiva will depend on the type of tooth that was in the site where the implant is now installed. FIGS. 3 and 4 illustrate a molar-type emergence-profiler abutment guide 50, for use as a healing component, having a mesial-distal dimension "L" and a buccal-labial dimension "W" which are characteristic of that type. A hole 52 through this abutment guide has the same diameter "D" as the core component 10. In use the healing component 50 is forced over the core component 10 so that the ribs 12 become embedded in the walls of the hole 52 until the healing component is seated on the shoulder 38. The assembly of both components is then attached to the implant in known fashion, using an abutment screw 54. The core component 10 is thereby fixed non-rotatively on the implant 20, and the healing component 50 is thereby fixed non-rotatively on the core component.

Figure 5:
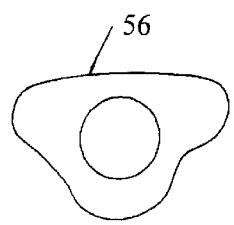
FIG. 5 is a top view of another emergence profiler component.

As is apparent in FIGS. 3 and 4, the healing component is now fixed in a position to force the aperture 46 to heal in a contour which closely replicates the emergence profile of a premolar-type tooth. FIG. 5 illustrates an alternative healing component 56 that can be used for restoration of another type tooth. It will be apparent that pairs of such tooth-shaped components can be provided at low cost in a wide variety of shapes, contours and sizes for a wide variety of tooth types.

Figure 6:
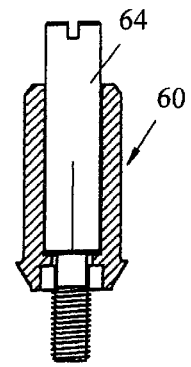
FIG. 6 is a longitudinal section through a core abutment for use as a pick-up type transfer coping.

Referring now to FIGS. 6 and 7, the invention is there illustrated as it may be used to take an impression preparatory to making a laboratory model. A core abutment 60 intended for use as a pick-up type impression coping is longer than the core abutment 10, and a pick-up type coping screw 64 replaces the abutment screw 54. Otherwise the two core abutments are substantially identical. In use, the healing component 50 and its core component 10 are removed together, as a unit, from the implant 20, the longer core abutment 60 is non-rotatively attached to the implant with the coping screw, and a second premolar-type emergence-profiler guide 50', intended for use as an impression coping component, which may be identical to the first premolar-type component 50, is fitted over the core abutment 60 engaging the ribs 62 while oriented identically to the healing component 50. This assembly 50'–60 can then function as a pick-up impression coping in know fashion. The protruding supragingival end of the core component 60, together with the portion of the emergence-profiler guide 50' which extends above the gum 44, will serve to retain the coping in the impression material (not shown). The coping screw 64 will extend through the impression tray (not shown) where it can be accessed to separate the impression coping assembly 50'–60 from the implant, allowing the coping assembly to be "picked-up", or retained in the impression for use in making a model of the site.

Figures 8, 9:
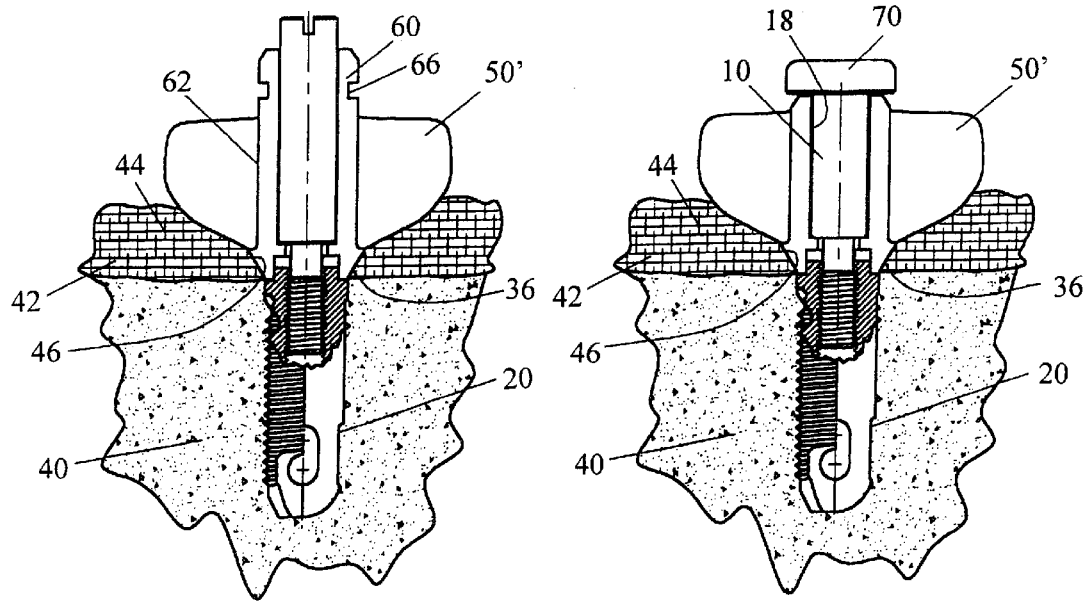
FIG. 8 is another embodiment of a pick-up transfer coping.
FIG. 9 shows another transfer coping according to the invention.
Figure 10:
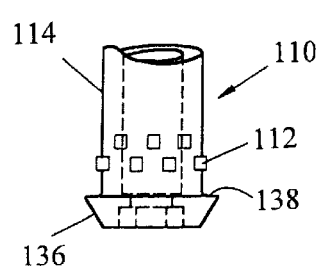
FIG. 10 is a side view of another core component.
Figure 11:
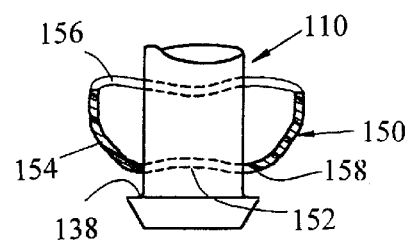
FIG. 11 is a section through another embodiment of the profiler guide.

Additional means to retain the pick-up coping assembly in impression material may be provided, in the form of an annular groove 66 on the core abutment 60, as is shown in FIG. 8, for example. In this embodiment, the groove 66 is preferably located closely above the top surface of the impression coping component 50', where impression material that flows into the groove can serve to lock the coping component 50' in place on the core abutment. Another alternative is to employ the shorter abutment 10 with a wide-headed impression-coping screw 70, like that shown in Pat. No. 4,955,811 owned by the assignee of this application, as is illustrated in FIG. 9. In this embodiment the transfer coping that results is not a pick-up coping. FIGS. 10 and 11 illustrate another embodiment of the invention employing a hollow-shell form 154 to make the emergence-profiler guide member 150 of the invention. The shell form can be, for example, blow-molded of a plastics material with an outer shape and contour to mimic a natural tooth. The shell has a round hole 152 in its bottom 158 through which a core component 110 can pass. Like the bore 52 in FIG. 4, this hole 152 has a diameter sized to fit closely around the core component. In use the shell 154 is fitted onto the core component 110 with its bottom 158 seated on the shoulder 138 on the subgingival end 136 and the shell is then filled, preferably to its rim 156, around the tubular part of the core component, with a flowable filling material such as an acrylic (not shown) intended for dental use, which hardens to form a substantially solid body within the shell, thereby providing a substantially solid emergence-profiler guide. The use of a flowable filling material allows the core component 110 to have multi-dimensional locking means such as projections 112 on its outer surface 114. Except for this unique difference the core component may be identical to the core components 10 or 60.

The invention thereby provides a new, accurate and inexpensive method and means for making and using an impression coping that faithfully reproduces the emergence profile established in the gingiva by the healing abutment component, and that can faithfully and accurately transfer that information to a working model in order to build an anatomically-shaped artificial tooth on a round-shaped implant.

The invention lends itself to the provision of temporary dentition. For example, the healing abutment can also function as a temporary tooth, albeit one lacking an occlusal surface. If an occlusal surface is desired the dentist can provide one by adding temporary tooth material (e.g: acrylic) to the top surface of the emergence-profiler guide 50.

We claim:

1. An abutment for attachment to a dental implant having a threaded bore, comprising:

a core having an internal bore for receiving a screw that is inserted into said threaded bore of said dental implant;

an outer component placed around said core, said outer component being polymeric and having a lower surface to be positioned near said implant and an upper surface to be positioned near an exterior gingival surface; and material for forming a temporary tooth attached to said upper surface of said outer component.

2. The abutment according to claim 1 wherein said core is substantially tubular and said outer component has a substantially cylindrical hole enabling said outer component to fit telescopically on said core.

3. The abutment according to claim 2 wherein said core has means for engaging a wall of said cylindrical hole for holding said outer component against rotation on said core.

4. The abutment according to claim 3 in which said engagement means comprises at least one longitudinal rib extending radially outward from said core.

5. The abutment according to claim 1 wherein said core includes structure to restrain said outer component from rotation therearound.

6. The abutment according to claim 1 wherein said core includes a radially extending flange at a lower portion thereof, said lower surface of said outer component resting on said flange.

7. The abutment according to claim 1 wherein said outer component is acrylic.

8. The abutment according to claim 1 wherein said outer component has a non-circular external shape substantially approximating a general shape of said natural tooth.

9. The abutment according to claim 1 wherein said outer component is modifiable by a clinician.

10. The abutment according to claim 1 wherein said core is metallic.

11. The abutment according to claim 1 wherein said outer component is made from at least two separate pieces, one of said pieces being a shell structure, the other of said pieces being a fill material placed within said shell structure.

12. The abutment according to claim 11 wherein said fill material is acrylic.

13. The abutment according to claim 12 wherein said temporary tooth material is acrylic.

14. The abutment according to claim 1 wherein said outer component is a unitary structure.

15. A healing abutment for attachment to a dental implant having a threaded bore, said healing abutment capable of supporting a temporary tooth, comprising:

a core having an internal bore for receiving a screw that is inserted into said threaded bore of said dental implant; and an outer component surrounding said core, said outer component being polymeric and having a lower surface to be positioned near said implant and an upper surface to be positioned near an outer gingival surface, said outer component having an exterior surface for engaging gingiva and forming said gingiva into a desired shape, said upper surface being modifiable by a clinician and for receiving material for forming a temporary tooth.

16. The abutment according to claim 15 wherein said core is substantially tubular and said outer component has a substantially cylindrical hole enabling said outer component to fit telescopically on said core.

17. The abutment according to claim 15 wherein said core includes a structure to restrain said outer component from rotation therearound.

18. The abutment according to claim 17 wherein said structure comprises at least one longitudinal rib.

19. The abutment according to claim 15 wherein said outer component is acrylic.

20. The abutment according to claim 15 wherein said core includes a radially extending flange at a lower portion thereof, said lower surface of said outer component resting on said flange.

21. The abutment according to claim 15 wherein said core is metallic.

22. The abutment according to claim 15 wherein said outer component is made from at least two separate pieces, one of said pieces being a shell structure, the other of said pieces being a fill material placed within said shell structure.

23. The abutment according to claim 15 wherein said outer component is a unitary structure.

24. An abutment for attachment to a dental implant comprising:

a core with a lower surface for engaging said implant and a tubular portion extending in a direction away from said lower surface, said tubular portion for receiving a screw for insertion into said dental implant; and an outer component for fitting around said tubular portion and being made of a material that is modifiable by a clinician at chair-side, said outer component being held non-rotationally on said tubular portion, said outer component having a gingival portion for extending through said gingiva, said gingival portion including an occlusal surface to be positioned adjacent to an exterior surface of said gingiva and for receiving material for forming a temporary tooth.

25. The abutment according to claim 24 wherein said outer component is a polymeric material.

26. The abutment according to claim 25 wherein said polymeric material is acrylic.

27. The abutment according to claim 24 wherein said outer component is made from at least two separate pieces, one of said pieces being a shell structure, the other of said pieces being a fill material placed within said shell structure.

28. The abutment according to claim 24 wherein said outer component is a unitary structure.

29. The abutment according to claim 24, wherein said tubular portion has a non-circular cross-section for effecting said non-rotational engagement with said outer component.

30. A method of developing a temporary tooth to be attached to a dental implant that is installed in a jawbone having overlying gingiva, said overlying gingiva having an aperture extending therethough that exposes said dental implant, comprising:

fitting an abutment into said aperture, said abutment having a metallic core with a lower surface for engaging said implant and a tubular portion extending in a direction away from said lower surface, said abutment further having an outer component for fitting around said tubular portion and being made of a first material that is modifiable by a clinician at chair-side, attaching said abutment to said dental implant;

adding a second material to an occlusal surface of said outer component; and forming said material into a temporary tooth.

31. The method of claim 30, wherein said first and second materials and said outer component are acrylic.

32. The method of claim 30, further including the step of modifying the outer component to the prevailing conditions of the patient's mouth, prior to said step of adding material.

* * * * *